(12) United States Patent
Cahill et al.

(10) Patent No.: US 8,372,876 B2
(45) Date of Patent: Feb. 12, 2013

(54) METHOD FOR IMPROVING MEMORY IN MAMMALS

(75) Inventors: Gregory M. Cahill, Houston, TX (US); Oliver Rawashdeh, Chicago, IL (US)

(73) Assignee: The University of Houston System, Houston, TX (US)

( * ) Notice: Subject to any disclaimer, the term of this patent is extended or adjusted under 35 U.S.C. 154(b) by 436 days.

(21) Appl. No.: 12/043,688

(22) Filed: Mar. 6, 2008

(65) Prior Publication Data
US 2008/0221199 A1    Sep. 11, 2008

Related U.S. Application Data

(60) Provisional application No. 60/893,276, filed on Mar. 6, 2007.

(51) Int. Cl.
*A61K 31/405* (2006.01)
*A61K 31/404* (2006.01)
*A61P 25/00* (2006.01)

(52) U.S. Cl. ........ 514/419; 514/343; 514/411; 514/221; 514/389; 514/561

(58) Field of Classification Search .................. 514/419, 514/343, 221, 389, 561, 411, 415
See application file for complete search history.

(56) References Cited

U.S. PATENT DOCUMENTS

2005/0164987 A1*  7/2005  Barberich ................... 514/58
2006/0229340 A1* 10/2006  Zisapel et al. ............... 514/343

* cited by examiner

*Primary Examiner* — Savitha Rao
(74) *Attorney, Agent, or Firm* — Robert W Strozier

(57) ABSTRACT

A method for improving memory in healthy subjects is disclosed. This method makes use of melatonin receptor antagonists such as luzindole and/or K-185 to reverse the inhibitory effect of melatonin. This invention is particularly relevant among subjects that do not show signs of central nervous system disorders and wish to improve their cognitive performance, especially in tasks.

16 Claims, 8 Drawing Sheets

METHOD FOR IMPROVING MEMORY IN MAMMALS

RELATED APPLICATIONS

This application claims priority of U.S. Provisional Patent Application Ser. No. 60/893,276, filed Mar. 6, 2007.

GOVERNMENTAL SPONSORSHIP

The U.S. Government has a paid-up license in this invention and the right in limited circumstances to require the patent owners to license others on reasonable terms as provided for by the terms of Contract No. 5 R01 MH069743-04 awarded by the National Institute of Mental Health.

BACKGROUND OF THE INVENTION

1. Field of the Invention

The present invention relates generally to a method for improving memory in mammals including humans by administering to the mammal a composition including at least one melatonin receptor antagonist, where the composition reverses inhibitory effects of melatonin in the mammal.

More particularly, the present invention relates a method for improving memory in healthy mammals including humans by administering to the mammal a composition including at least one melatonin receptor antagonist, where the composition reverses inhibitory effects of melatonin in the mammal permitting enhanced learning and/or post learning performance of cognitive learning activities such as studying, task oriented training, or the performance of any other task or skill that has a cognitive memory component thereto.

2. Description of the Related Art

A variety of over-the-counter substances are said to improve memory, including herbs and supplements, with little evidence of efficacy and little understanding of their mechanism of action. In addition to these supplements, some drugs have been developed to remediate deficiencies of the central nervous system, such as modafinil, methylphenidate, and dextroamphetamine. Some of these drugs are known to be occasionally used to improve the cognitive performance of healthy subjects, such as the use of dextroamphetamine among the military. These three above mentioned drugs are all stimulants that act by affecting norepinephrine and dopamine levels. The present invention however makes use of melatonin receptor antagonists as a method for improving memory in healthy subjects—defined as subjects that do not show signs of central nervous system disorders.

In mammals, melatonin has been implicated in the transduction of photoperiodic information, modulation of a variety of neuronal and endocrine functions, regulation of reproduction, metabolism, sleep, retina physiology, cardiovascular and immune functions, cancer cell growth and the control of circadian rhythms. Some studies have clarified the production of melatonin. Melatonin (5-$OCH_3$ N-acetyltryptamine) is the principal hormone produced by the pineal gland. The circadian oscillator of both the pineal gland and retina in most organisms studied to date have been shown to regulate melatonin synthesis, with increased melatonin production during the night and reduced melatonin synthesis during the day. For diurnal organisms such as humans and zebrafish, the period of increased melatonin production coincides with the organism's habitual hours of sleep and the onset of melatonin secretion correlates with the onset of evening sleepiness. The effects of melatonin, at least in part, are mediated through high affinity G protein-coupled melatonin receptors.

Membrane bound melatonin receptors are classified according to pharmacological and kinetic properties into two classes ($ML_1$ and $ML_2$). Three receptors with $ML_1$ pharmacological characteristics have been cloned in several vertebrate species including humans ($Mel_{1a}$ $Mel_{1b}$, $Mel_{1c}$). Mammalian melatonin receptors are now known as $MT_1$ for $Mel_{1a}$ and $MT_2$ for $Mel_{2b}$. Both $MT_1$ and $MT_2$ share 60% amino acid homology.

Luzindole (or N-Acetyl-2-benzyltryptamine) is one of several melatonin receptor antagonists. It is known to be a competitive melatonin antagonist that is effective in blocking melatonin receptors in brain and is active in vivo. Behavioral tests in C3H/HeN mice show that treatment with luzindole decreases the duration of immobility during swimming with a more pronounced effect at midnight, when endogenous melatonin levels are elevated as compared to midday time. Further studies suggest that luzindole may exert like an antidepressant by blocking endogenous melatonin mediated signaling in the central nervous system.

K-185 (or N-butanoyl-2-(5,6,7-trihydro-11-methoxy-benzo[3,4]cyclohept[2,1-a]indol-13-yl) ethanamine) is yet another type of melatonin receptor antagonist with over a 140-fold higher affinity for $MT_2$ than for $MT_1$ subtypes of melatonin receptors. However, the affinity kinetics and binding characteristics of K-185 and other melatonin receptors differ among animal types. K-185 has antagonizing effects to melatonin in some animal models, while K-185 shows partial agonistic characteristics in other animal models. Studies in zebrafish embryos reveal that K-185 has antagonistic properties by blocking the effect of melatonin on zebrafish development.

Prior to the development of melatonin receptor antagonists and even today, conventional methods for purposely regulating melatonin levels include (1) the use of an external bright light treatment, or (2) the removal of the pineal gland. Removal of the pineal gland may not significantly lower endogenous melatonin levels, as other melatonin producing sites such as the retina and digestive system exist and they may substantially contribute to modulating melatonin levels. However, with the availability of a competitive melatonin receptor antagonist such as luzindole, the classical methods in antagonizing endogenous melatonin levels such as bright light and pinealectomy can be mimicked. The advantage of using competitive melatonin receptors over conventional techniques is two fold: (1) it avoids the need for surgical interventions, such as pinealectomy, and (2) it probably has less effect on the circadian system than bright light does. Luzindole and other melatonin receptor antagonists have been used mainly in in vitro studies involving the localization or distribution and characterization of melatonin receptors in various tissues. However, to date no study has addressed the behavioral impact of melatonin receptor antagonists.

It is therefore the purpose of this invention to take advantage of the effect of melatonin receptor antagonists, including but not limited to luzindole and/or K-185, particularly with regards to improving memory in healthy subjects.

SUMMARY OF THE INVENTION

The present invention provides a method for improving memory in mammals including humans including administering an effective amount of a melatonin receptor antagonist or a mixture thereof to an animal including a human, where the effective amount is sufficient to improve memory.

The present invention also provides a method for improving memory in mammals including humans including administering an effective amount of a melatonin receptor antagonist or a mixture thereof to an animal including a human, where the effective amount is sufficient to improve memory for a desired task.

The present invention also provides a method for improving memory in mammals including humans including administering an effective amount of a melatonin receptor antagonist or a mixture thereof to an animal including a human, where the effective amount is sufficient to improve memory and/or cognitive performance of a desired task.

BRIEF DESCRIPTION OF THE DRAWINGS

The invention can be better understood with reference to the following detailed description together with the appended illustrative drawings in which like elements are numbered the same.

DETAILED DESCRIPTION OF THE INVENTION

Figure 1A:
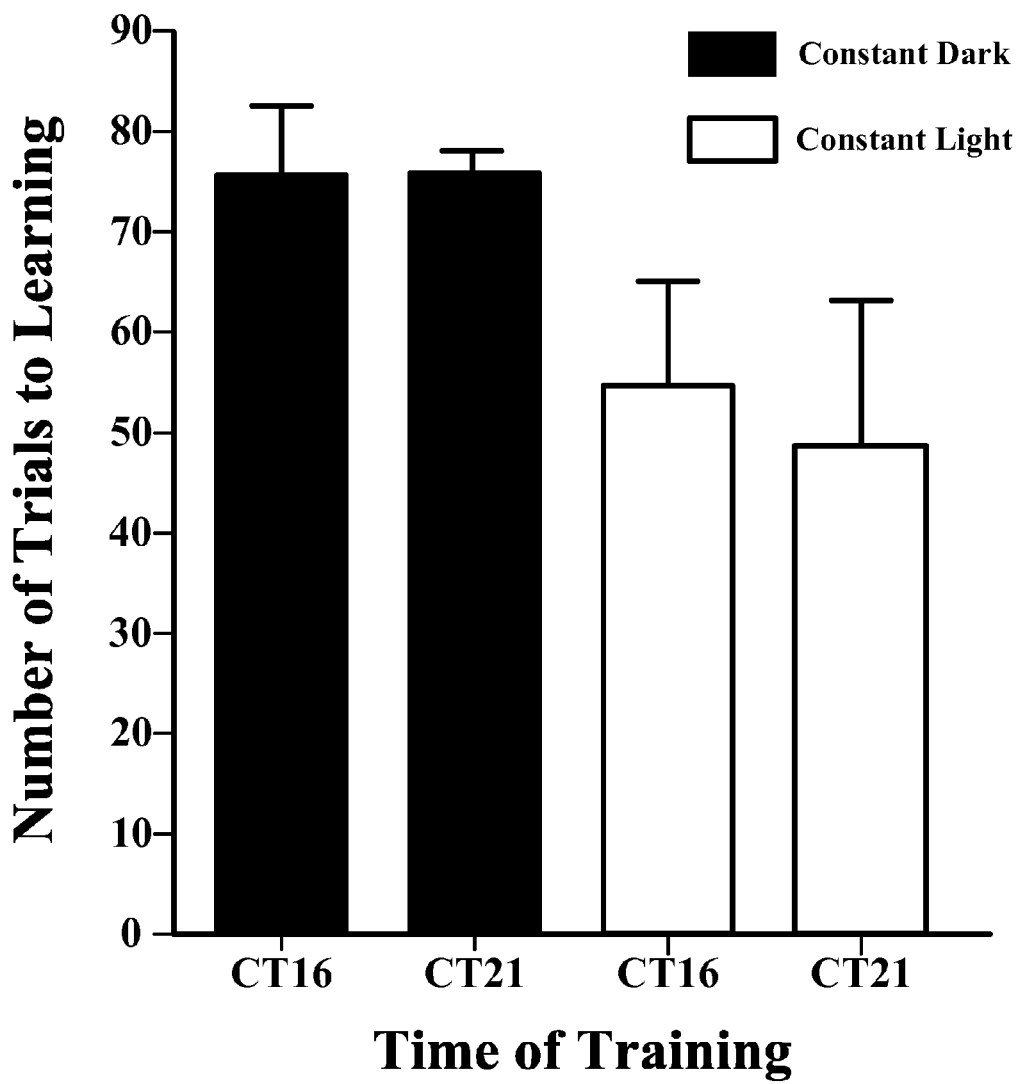
FIG. 1a shows the number of trials necessary to achieve the learning criteria (i.e. swimming the compartment where the stimulus light was on and remain there until the light was switched off) for animals trained during the subjective night (CT16 and 21), in the case where animals are subjected to either constant darkness (black bars) or constant light (white bars). Comparison of the number of trials to learning was not significantly different ($F_{(3,24)}=1.898, p>0.1$) when animals are subjected to constant darkness compared to constant light ($F_{(3,24)}=1.898, p>0.1$).

The inventors have found that a melatonin receptor antagonist or a mixture of melatonin receptor antagonists (e.g., luzindole, K-185, etc.) are effective for improving memory when administered at a dosing level, a dosing time and a dosing duration designed to achieve a desired improvement in long term memory, especially memory associated with learned behavior or learning exercises. In certain embodiments, the inventors have found that the melatonin antagonists can be used in healthy subjects to improve the retention of learned behavior in cognitive learning activities and to improve performance of the learned activities in associated cognitive tasks. The inventors believe that the compositions will find application in improving the performance of mammals including humans in tasks that rely on memory retention for improved performance of the task. The tasks generally would include, without limitations, learning cognitive activities such as students studying for examinations, training of canines for use in civil and military applications, training of in task, where memory of data concerning the task is critical, such as sports, military operations, police operations, police investigations, etc. or in any other application where memory retention plays a vital role in the successful performance of the task.

The present invention broadly relates to a method for improving memory in mammals including humans including administering an effective amount of a melatonin receptor antagonist composition to an animal including a human, where the effective amount is sufficient to improve memory. In certain embodiments, the effective amount is sufficient to improve memory for a desired task. In other embodiments, the effective amount is sufficient to improve memory and/or cognitive performance of a desired task. In other embodiments, dose is increased to further enhance and/or augmented cognitive performance of a desired task. In all of these embodiments, the melatonin receptor antagonist composition includes luzindole, K-185 or a mixture of luzindole and K-185. In all of these embodiments, the melatonin receptor antagonist compositions can include carriers, excipients, adjuvants, buffers, other pharmaceuticals that do not interfere with the memory augmenting or enhancing attributes of the compositions. In all of the embodiments, the compositions can be in the form of pills, tablets, capsules (solid, soft shell, hard shell, etc.), syrups, liquids, patches, films, injectables, or any other suitable form for administration. In all of these embodiments, the administration can be oral, topical (patches), injection (i.v., arterial, direct, etc.), nasal, eye drops, rectal, vaginal, or any other administration format.

The inventors have found that the memory enhancing compositions of this invention are generally administered in a dose range between about 1 mg/kg to about 1000 mg/kg. In certain embodiments, the dose range is between about 1 mg/kg to about 500 mg/kg. In other embodiments, the dose ranges is between about 1 mg/kg to about 100 mg/kg. In other embodiments, the dose ranges is between about 5 mg/kg to about 100 mg/kg. In other embodiments, the dose ranges is between about 10 mg/kg to about 100 mg/kg. In other embodiments, the dose ranges is between about 20 mg/kg to about 100 mg/kg. However, smaller and larger doses are envisioned.

The inventors have also found that the memory enhancing compositions of this invention are generally administered for a short time before and possibly during the learning phase leading up to the performance of a task having a cognitive and memory aspect. The inventors believe that the composition are to be take prior to engaging in a cognitive learning activity, prior to sleep after engaging in a cognitive learning activity, or prior to the cognitive learning activity and prior to sleep after the cognitive learning activity. Generally, the compositions should be take within an hour of commencing the activity and/or going to sleep after the cognitive learning activity. In certain embodiment, the composition should be taken about 45 minutes prior to commencing the activity and/or going to sleep after the activity. In certain embodiment, the composition should be taken about 30 minutes prior to commencing the activity and/or going to sleep after the activity. However, shorter or longer times are covered as well.

The administration of the compositions of this invention to mammals including humans is designed to enhance task performance by enhancing the reduction of learned behavior to recallable memory. This enhancement results in enhanced performance of task after the learning period has been completed. Thus, the administration is transient and temporally localized to a period of intense and focused learning of one or more specific patterns, behaviors, tasks, exercises, or the like to enhance recall of the learned patterns, behaviors, tasks, exercises or the like. Such enhanced recall translating into improved performance, improved outcomes and likely improved safety.

Memory Model

In order to evidence the memory enhancing properties of the compositions of this invention, the inventors performed experiments on zebrafish, where memory is easily assessed. The zebrafish is a powerful model system due to its low cost, rapid in vivo analysis and complex vertebrate biology. The advantages of zebrafish over other model systems lies in its optical clarity in a vertebrate embryo amenable to large-scale screening, including genetic and small molecule drug screening. Zebrafish are related evolutionary closer to humans than yeast, insects or worms. Zebrafish genes share on average more than 75% similarity to human genes. To date, the characterization of zebrafish mutants has repeatedly demonstrated that mutations in zebrafish orthologous to human disease genes produce phenotypes similar to human diseases. Due to strong biological conservation between zebrafish and humans, various drugs used on zebrafish show similar effects on humans. Furthermore, knocking down certain genes in zebrafish, similar to genes found in humans, and known in humans to be involved in some physiological malfunctioning when found in a mutated form; result in similar phenotypes. Furthermore, from a circadian perspective, both zebrafish and humans are diurnally active and have similar melatonin rhythm profiles with increased levels of melatonin during the night as compared to daytime melatonin levels. The National Institute of Health (NIH) that ranks developmental systems for research found zebrafish to be third, behind humans and mice.

Animals Protocols

Zebrafish (*D. rerio*) were bred, raised and maintained by the experimenter at the University of Houston Animals Facility. Adult zebrafish are maintained in 2-liter modular aquaria (Marine Biotech) with continuous water exchange at 26-28° C. under 14:10 hours light:dark cycle. Eggs and larvae are maintained in beakers with daily water changes, under the same light:dark cycle and similar temperatures. Larval fish are fed with filtered paramecium. All animals, juvenile (>15 days) and adults are fed three times a day with live brine shrimp or flake. The *AB strain was originally obtained from the University of Oregon. All protocols were approved by the University of Houston Institutional Animal Care Use Committee.

Behavioral Training and Testing

Conditioning

Zebrafish are trained on an active-avoidance conditioning paradigm using a modified shuttle box. Zebrafish must cross a hurdle to avoid electric shocks (3V; unconditioned stimulus) administered via electrodes 10 seconds after the onset of the conditioned stimulus which was a dim red light. Dim red lights are placed at the extremity of each compartment of the shuttle box. The light signal was kept on during each cycle lasting for 20 seconds in one compartment; subsequently, the conditioned and unconditioned stimuli changed to the other side of the shuttle box.

By convention, the onset of activity of diurnal organisms defines circadian time zero (CT 0). The onset of activity of nocturnal organisms defines circadian time twelve (CT 12). The subjective day was defined as the segment of a circadian cycle during the freerun state that corresponds to the illuminated segment during entrainment by a light-dark cycle. Metaphorically, the organism "thinks" that subjective day was the daylight segment of a day. The subjective night was defined as the segment of a circadian cycle during the freerun state that corresponds to the dark segment during entrainment by a light-dark cycle. Metaphorically, the organism "thinks" that subjective night was the night segment of a day.

Learning

Zebrafish must learn to escape the dark compartment and maintain in the compartment having the light stimulus on for the remaining trial period. Animals that respond correctly to the light signals in eight out of ten consecutive trials during the training period are designated learners. Training was terminated once Zebrafish achieve the learning criteria (i.e. swimming the compartment where the stimulus light was on and remain there until the light was switched off). Animals that do not achieve the learning criteria within 30 minutes after the onset of training are removed from the experiment.

Testing

Animals are tested 24 hours later under identical conditions to test for retention of the learned task. To quantitatively evaluate the ability of each learner to recall the active avoidance conditioning paradigm, a retention score was calculated using the algorithm of Piront and Schmidt $$RS = \frac{(\text{Trials to criteria(train)} - 8) - (\text{Trials to criteria(test)} - 8)}{(\text{Trials to criteria(train)} - 8) + (\text{Trials to criteria(test)} - 8)}$$

The number of trials required to reach the learning criteria during the test session was subtracted from number of trials required to reach the learning criteria in the training session, divided by the number of trials in the test plus training sessions. Retention scores range from 0 to 1.0. A score of 1.0 corresponds to animals recalling the learning paradigm immediately without receiving a shock, whereas a score of 0.0±0.2 corresponds to animals that do not recall the learned task.

Melatonin Blocks Long-Term Memory Formation During the Subjective Day

One embodiment of the present invention was that melatonin blocks long-term memory formation during the subjective day. This was successfully tested by lowering night time melatonin levels by direct exposure to constant light. Such conditions help consolidate acquisition for active avoidance conditioning during the subjective night. However, animals set under free-running conditions of constant darkness and temperature showed long-term memory formation when trained during the subjective day but not when trained during the subjective night (i.e., when physiological levels of melatonin are high).

In one set of experiments, zebrafish were conditioned to live under constant light, trained during subjective night and tested 24 hours later during subjective night. This conditioning was achieved by taking animals that have previously kept in 14:10 hours light/dark cycles and condition them in days of continuous light, 24 hours a day. On the third day of constant light on, animals were trained during the subjective night at circadian time 16 (CT16) and CT21 (corresponding to 12 am and 5 am respectively) when physiological levels of melatonin in zebrafish were high. Animals were then tested for long-term memory formation 24 hours during subjective night at CT16 and CT21. Animals were not fed during the 4 days of constant light in order to maintain constant conditions.

In another set of experiments, zebrafish were conditioned to live under constant darkness, trained and tested during the subjective night. On the third day of constant darkness, animals were trained during the subjective night at CT16 and CT21 (corresponding to 12 am and 5 am respectively). Animals were then tested for long-term memory formation 24 hours later at CT16 and CT21. Animals were not fed for the duration of 4 days during which the animals were in continuous darkness.

Figure 1B:
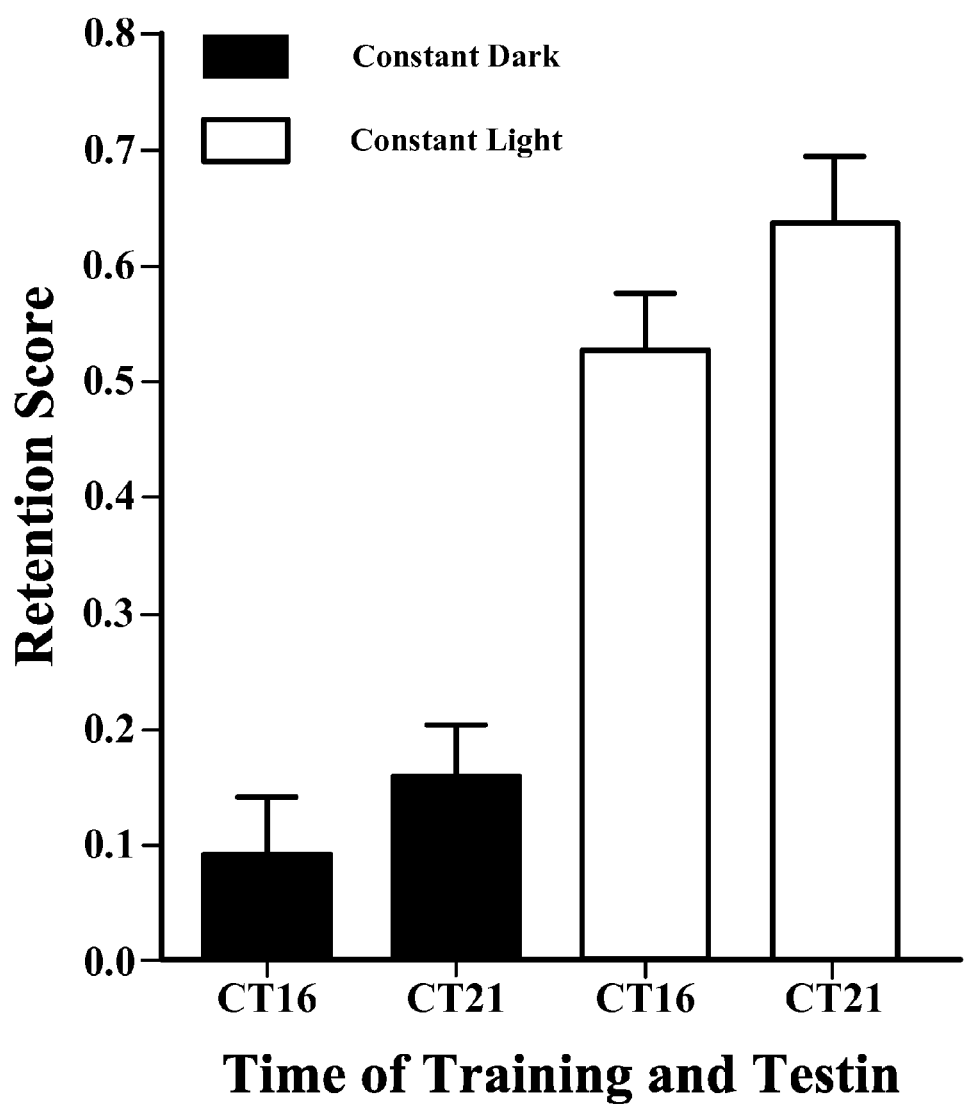
FIG. 1b shows the retention score (i.e. measurement of memory formation) of the learned task 24 hours after the learning period under the same conditions in the case where animals are subjected to either constant darkness (black bars) or constant light (white bars). Animals trained under constant light conditions during the subjective night show a significant increase in retention scores compared to animals trained under constant darkness during the subjective night ($F(3,23)=25.22, p<0.0001$, Newmann-Keuls post hoc analysis $p<0.001$ for CT16 constant light v. CT16 and CT21 constant darkness, $p<0.01$ for CT21 constant light v. CT21 constant darkness and $p<0.001$ for CT21 constant light v. CT16 constant darkness)

FIG. 1b shows that when animals were conditioned to live under constant light, long-term memory was acquired as retention scores were high (typically above 0.55). On the other hand, animals that were conditioned to live under constant darkness (when physiological levels of melatonin were high) do not demonstrate long-term memory formation as retention scores were low (below 0.2). This means that melatonin was directly involved in memory retention, i.e., high levels of melatonin inhibited memory retention, hence reduced cognitive performance. The rhythm of long-term memory formation was regulated or modulated by the zebrafish's circadian system.

Furthermore, FIG. 1a shows that the number of trials to learning was not significantly affected by training conditions, i.e. whether zebrafish were trained during the night or during the day. In other words, these results suggest that learning, as opposed to memory, was not strongly affected by melatonin levels.

High Levels of Melatonin Suppress Long-Term Memory Formation

Figure 2A:
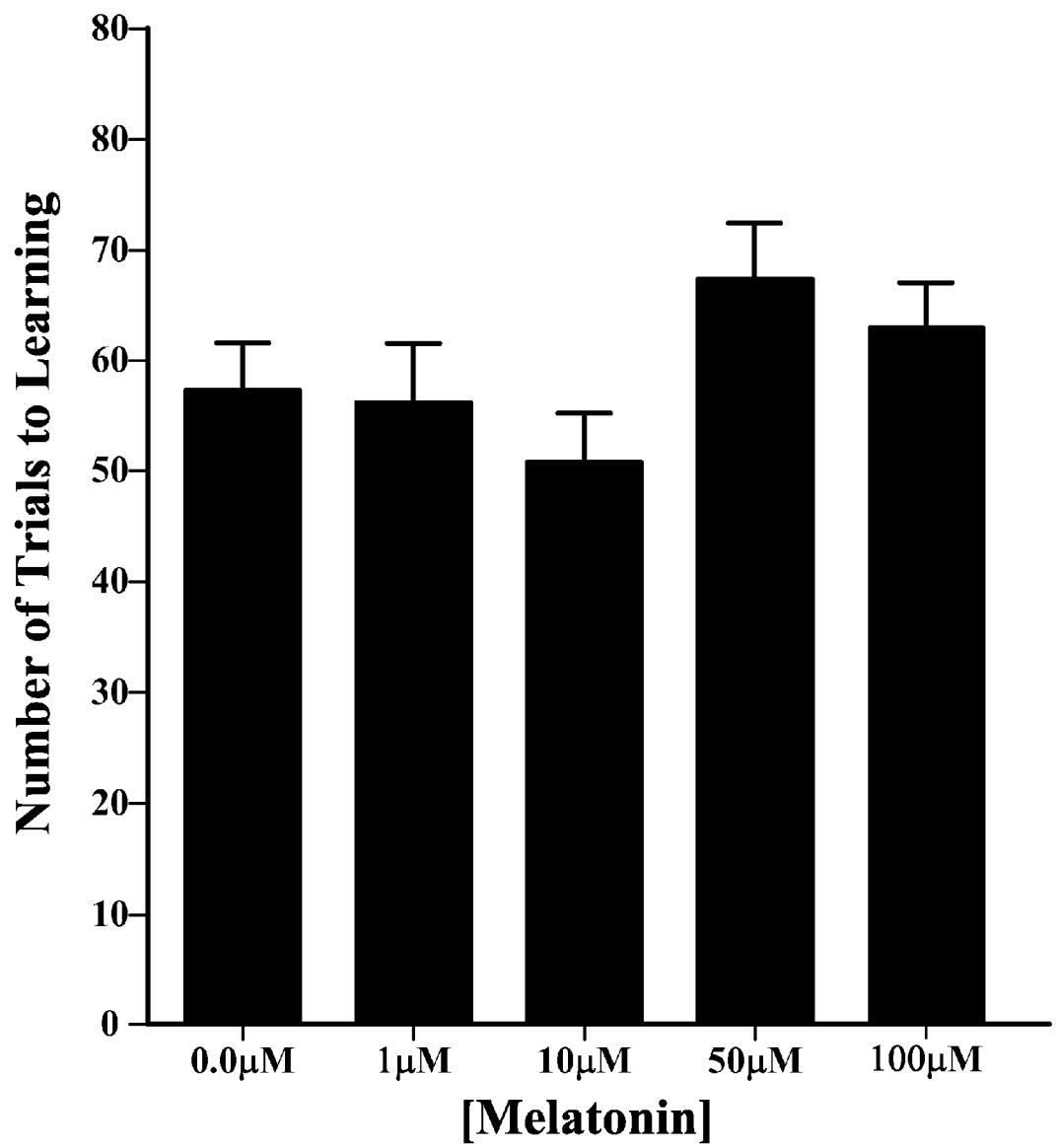
FIG. 2a shows the effect of 1 hour of melatonin treatment during the subjective day on learning at various concentrations (1 µM, 10 µM, 50 µM, and 100 µM) of melatonin. No significant difference in the number of trials necessary to reach the learning criteria was observed between the different concentrations of melatonin ($F_{(4,41)}=1.859, p>0.5$).
Figure 2B:
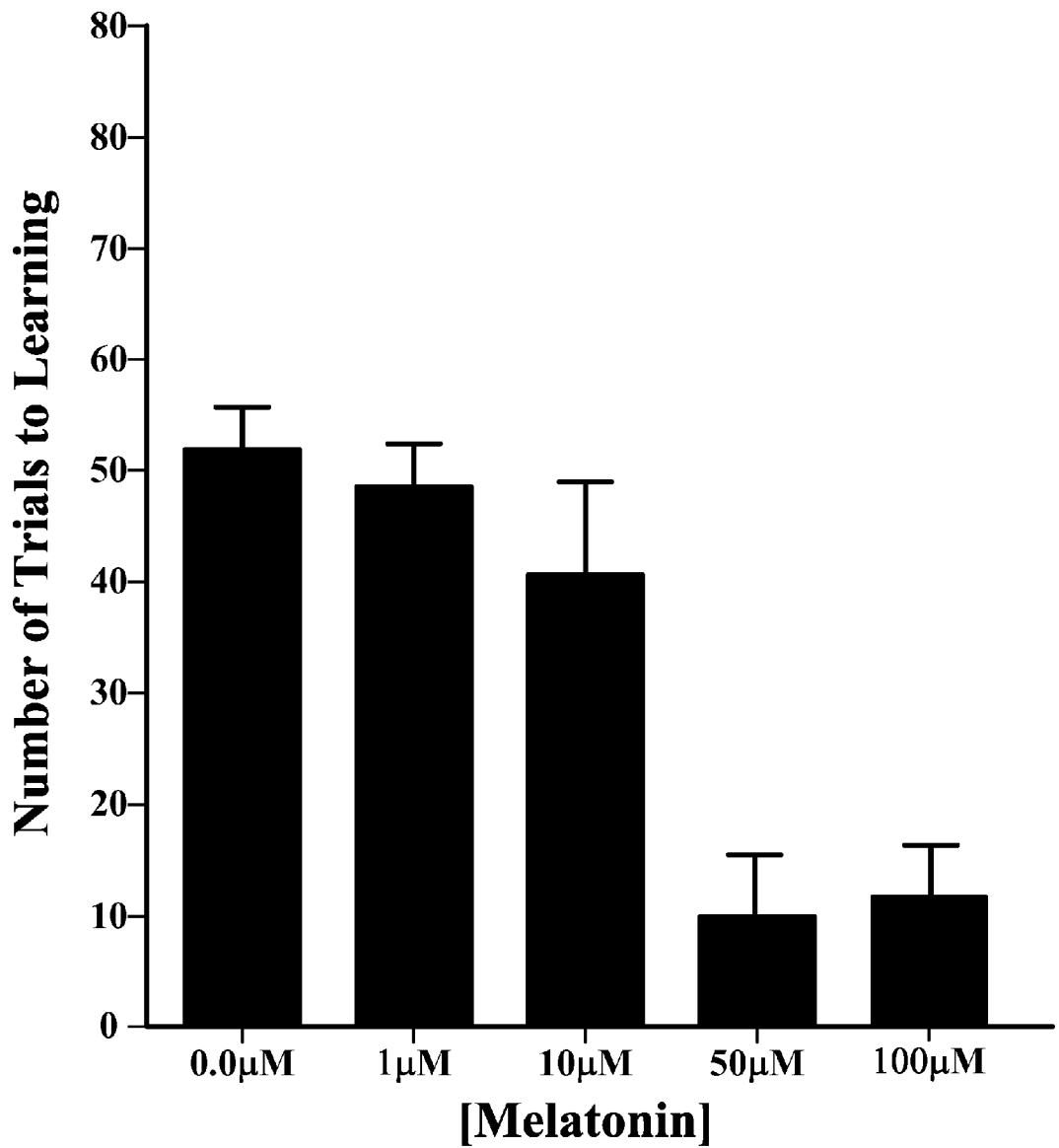
FIG. 2b shows the effect of 1 hour of melatonin treatment during the subjective day on retention scores at various concentrations of melatonin. Retention scores are significantly reduced at high concentrations (50 µM and 100 µM) of melatonin compared to lower melatonin concentrations and control ($F_{(7,56)}=8.624, p<0.0001$; Newmann-Keuls post hoc analysis $p<0.01$ for 50 µM v. control and $p<0.001$ for 100 µM v. control).

Another embodiment of the present invention is that high levels of melatonin suppress long-term memory formation. This melatonin effect was tested by taking animals originally under 14:10 hours light:dark cycles and exposing them to constant darkness for 4 days. On the $3^{rd}$ day of constant darkness and one hour prior to training at CT7 (corresponds to 4 pm) animals were bathed in increasing concentrations of melatonin (1 μM, 10 μM, 50 μM and 100 μM). Animals were then trained at CT8 for active avoidance conditioning and tested 24 hours later on the $4^{th}$ day of constant darkness at CT8 for long-term memory formation. FIG. 2a shows that treatment with melatonin does not affect acquisition at any of the melatonin concentrations tested (1 μM, 10 μM, 50 μM and 100 μM), as the number of trials to learning remains between 0.5 and 0.7, regardless of melatonin concentration.

On the other hand, when animals were tested for long-term memory formation 24 hours after training at CT8, it was evident that melatonin concentration over 50 μM significantly attenuated long-term memory formation during the subjective day, as retention scores (i.e., the ability to remember the learned task) remain around 0.1. However, low concentrations of melatonin do not significantly block long-term memory formation. These results show that (1) melatonin treatment during the day inhibit long-term memory formation, and (2) elevated night time physiological levels of melatonin in healthy subjects was likely to have a similar functional role in suppressing long-term memory formation for newly night time learned tasks.

The Inhibitory Effect of Melatonin on Long-Term Memory Formation is Mediated via Melatonin Receptor Signaling Pathway Another embodiment of the present invention is that the inhibitory effect of melatonin on long-term memory formation is mediated via melatonin receptor signaling pathway.

Figure 3A:
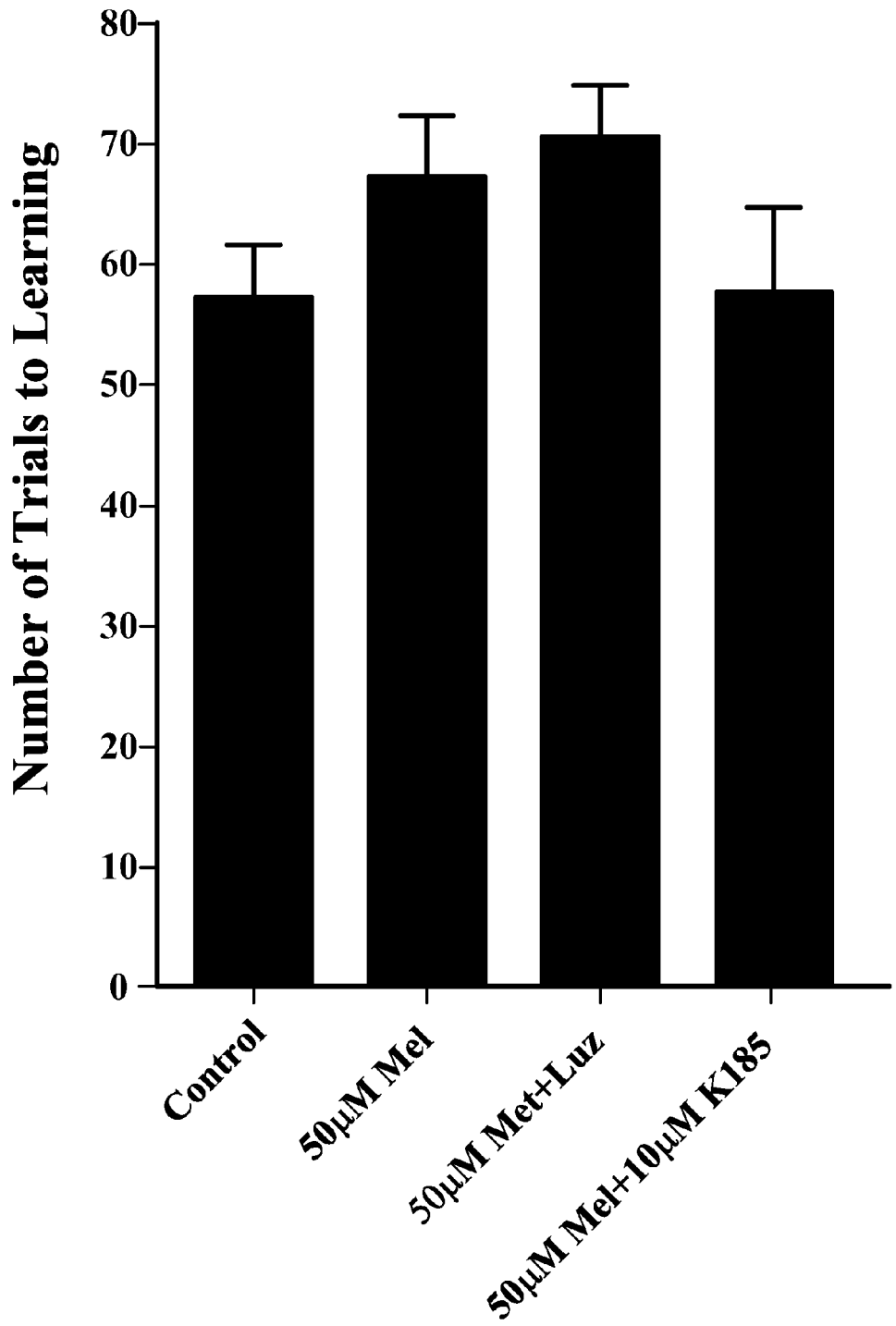
FIG. 3a shows the effect of 1 hour of treatment on learning using vehicle alone (0.4% ethanol), 50 µM of melatonin alone, 50 µM of melatonin in the presence of a 50 µM of luzindole, and 50 µM of melatonin in the presence of a 10 µM of K-185. No significant difference in number of trials to learning criteria was observed among the different groups ($F_{(3,24)}=1.973, p>0.1$).
Figure 3B:
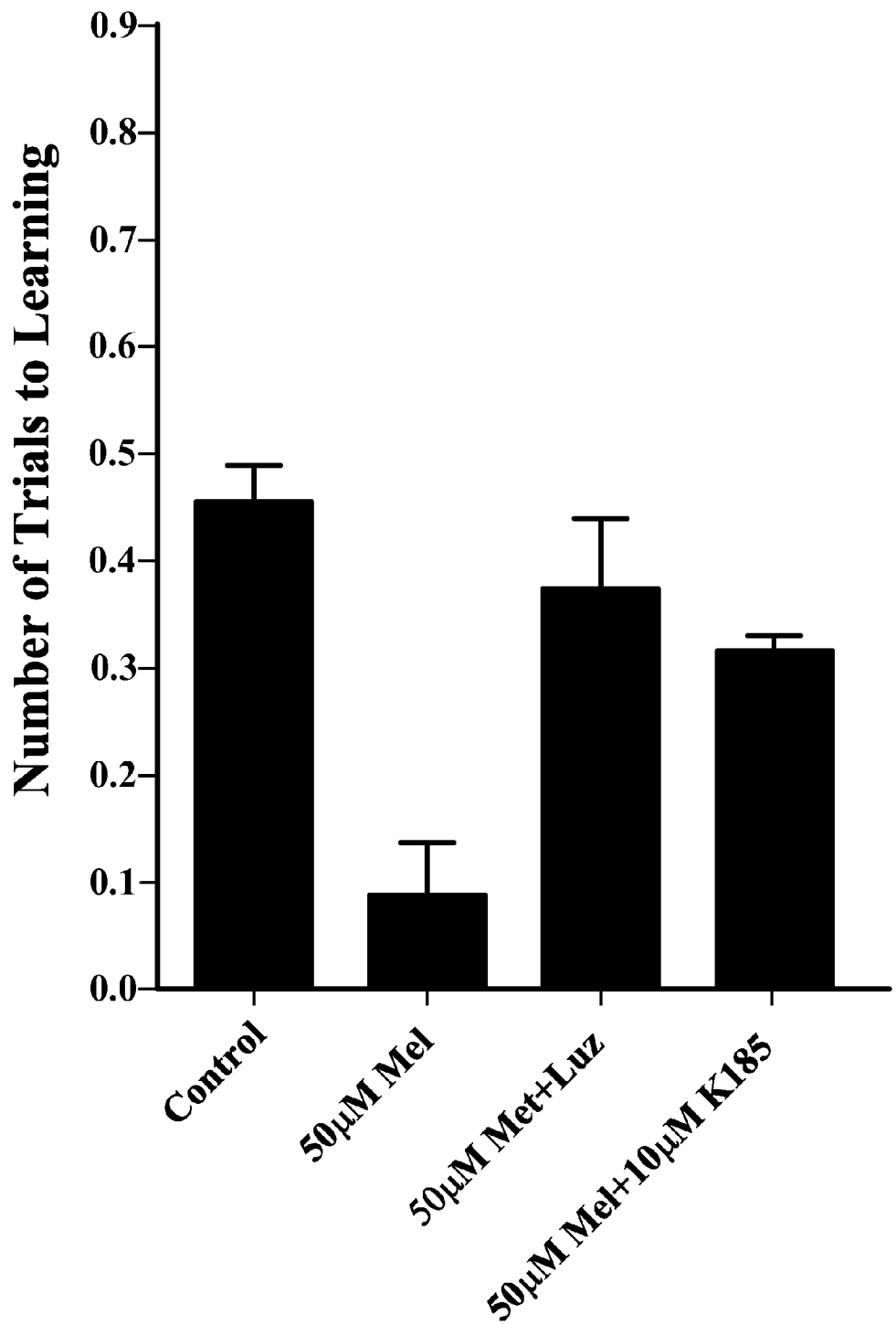
FIG. 3b shows the effect of 1 hour of treatment on retention score using vehicle alone (0.4% ethanol), 50 µM of melatonin alone, 50 µM of melatonin in the presence of a 10 µM of luzindole, and 50 µM of melatonin in the presence of a 10 µM of K-185. The groups of animals treated with melatonin in the presence of melatonin receptor antagonist (luzindole or K-185) do not significantly differ in their retention scores compared to the control (Newmann-Keuls post hoc analysis $p>0.05$, control v. 50 µM melatonin+50 µM luzindole and $p>0.05$, control v. 50 µM melatonin+10 µM K-185).

The experiments described above suggest that melatonin inhibits long-term memory formation according to (1) some unknown side effect, or (2) intracellular activation of an unknown signaling pathway due to its lipophylic characteristics, or (3) by melatonin receptor mediated signaling. To test whether melatonin blocks long-term memory formation via melatonin receptor mediated signaling pathway, the following experiments were performed. Animals in their original 14:10 hours light:dark cycles were set under free running conditions of constant darkness and temperature (25° C.) for 4 days. On the $3^{rd}$ day of constant darkness, four groups of animals were treated for one hour at CT7 with (1) vehicle alone (0.4%, ethanol), acting as control; or (2) 50 μM melatonin only; or (3) 50 μM melatonin in the presence of 50 μM luzindole (a melatonin receptor antagonist); or (4) 50 μM melatonin in the presence of 10 μM K-185 (another melatonin receptor antagonist). Animals were trained for active avoidance conditioning at CT8 and tested for long-term memory formation 24 hours later at CT8 on the $4^{th}$ day of constant darkness. FIG. 3a shows that neither of the four treatments has a significant effect on learning, as the number of trials to learning remains around 0.6-0.7, regardless of the chemicals present. However, FIG. 3b clearly indicates that long-term memory formation was significantly affected by the presence of melatonin, as the retention score was low, around 0.1. Treatments comprising of melatonin and either of its antagonists (luzindole or K-185) do improve the retention score, going from 0.1 with melatonin alone to about 0.4 in the presence of a mixture of melatonin and luzindole and to about 0.3 in the presence of a mixture of melatonin and K-185. These results indicate that melatonin receptor antagonists reverse the inhibitory effect of melatonin on long-term memory formation. This means that the inhibitory action of melatonin was mediated via a melatonin receptor-signaling pathway.

Long-term Memory Formation is Improved by Blocking Melatonin Receptor Mediated Signaling During the Subjective Night Another embodiment of the present invention is that long-term memory formation is improved by blocking melatonin receptor mediated signaling during the subjective night.

Figure 4A:
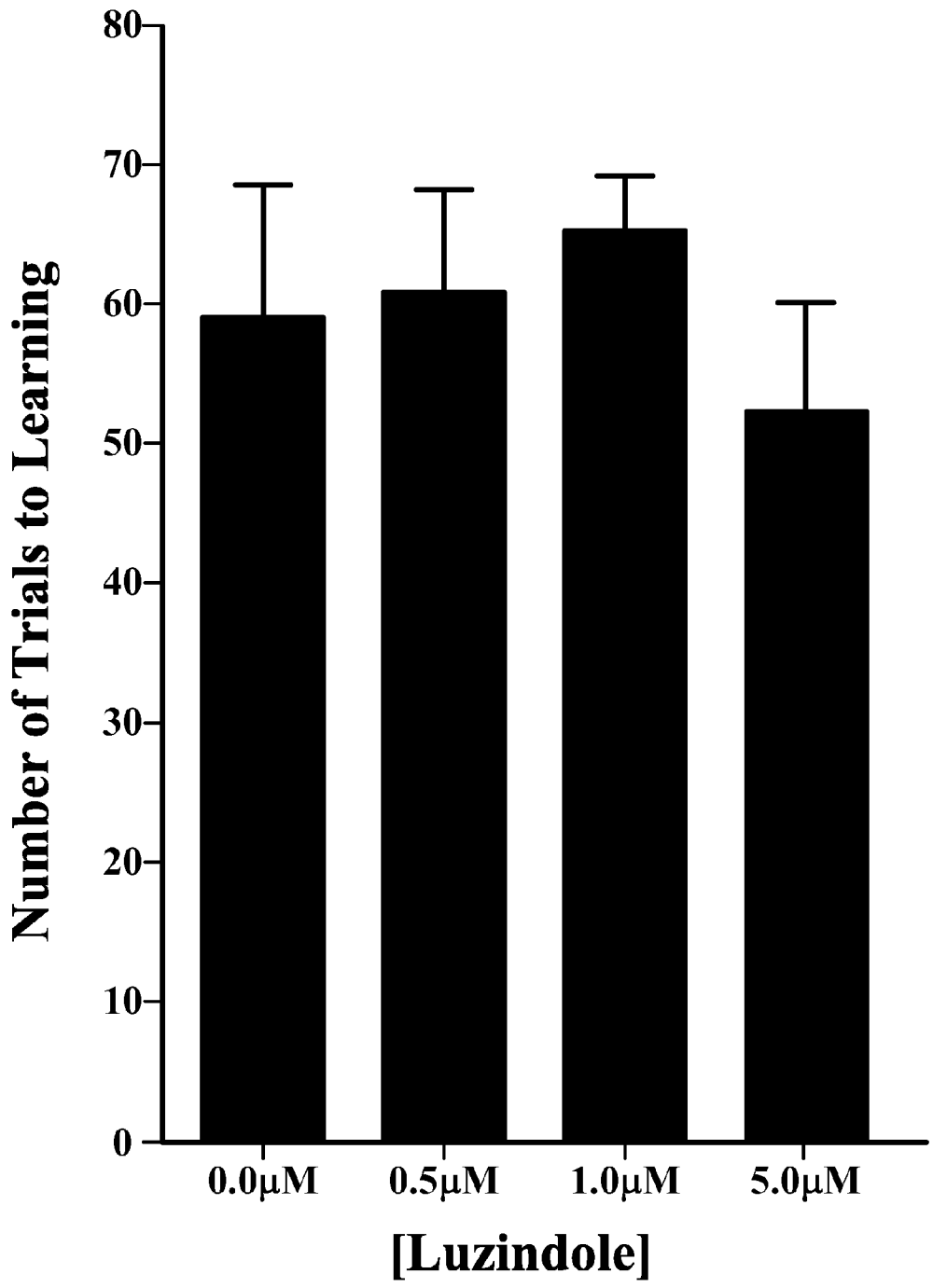
FIG. 4a shows the effect of 1 hour of treatment during the subjective night on learning using vehicle alone (0.4% ethanol) and four different concentrations (1 µM, 10 µM, 50 µM, and 100 µM) of luzindole. No significant difference in the number of trials to reach learning criteria was observed as luzindole concentration was increased ($F_{(3,15)}=0.5195, p>0.5$).
Figure 4B:
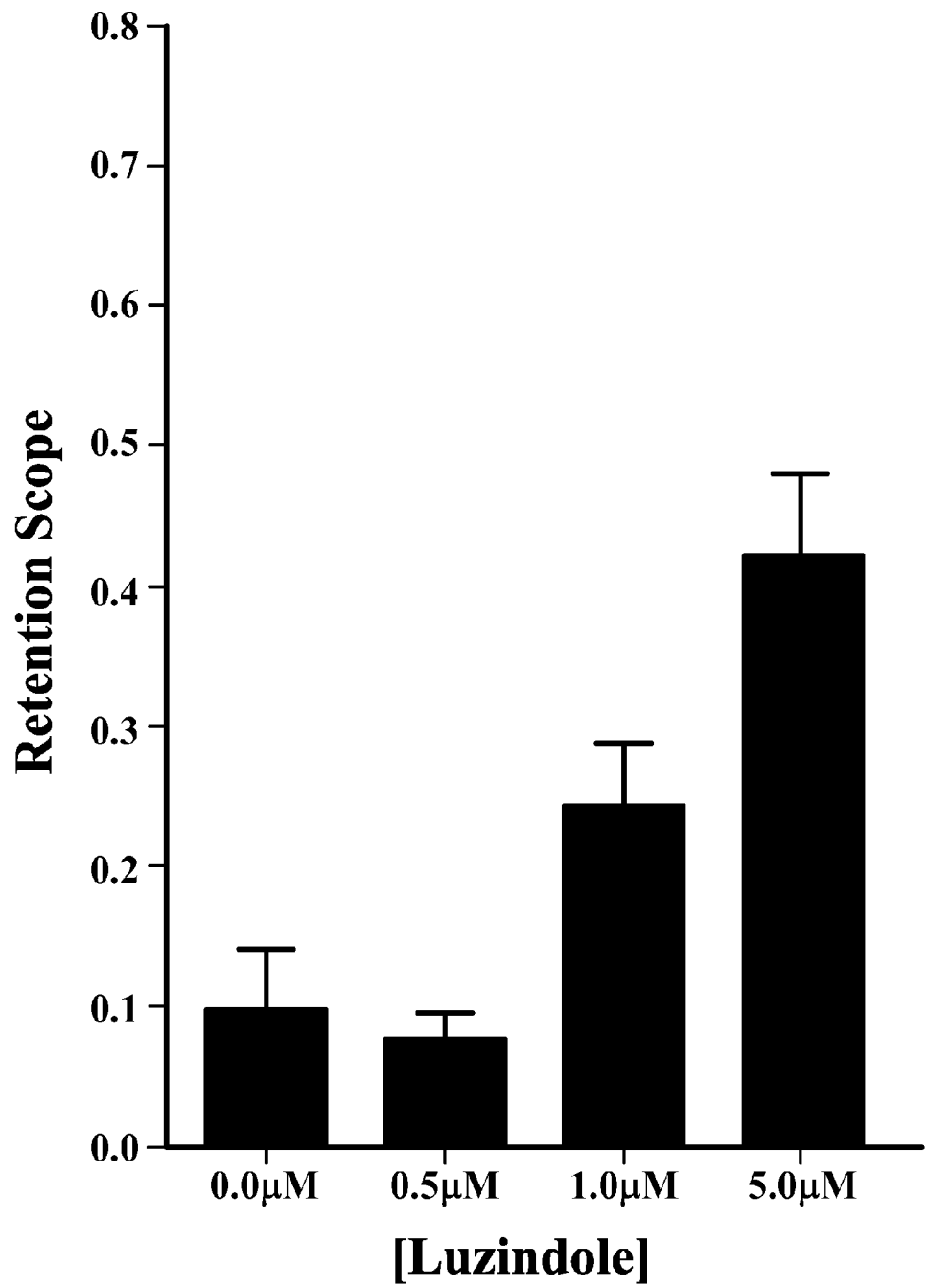
FIG. 4b shows the effect of 1 hour of treatment during the subjective night on retention score using vehicle alone (0.4% ethanol) and four different concentrations (1 µM, 10 µM, 50 µM, and 100 µM) of luzindole. Only animals treated with 5 µM luzindole demonstrate a significant improvement in long-term memory during the subjective night (Newmann-Keuls post hoc analysis $p<0.001$, 5 µM v. 0.0 µM and 0.5 µM and $p<0.05$, 5 µM v. 1 µM).

Having demonstrated that (1) melatonin blocks long-term memory formation during the subjective day, (2) the decrease of physiological levels of melatonin results in robust long-term memory formation, (3) the inhibitory action of melatonin on long-term memory formation was mediated via melatonin receptor signaling, led us to investigate whether physiological elevated night time melatonin levels can phenocopy the inhibitory action of melatonin on long-term memory formation. This effect was tested by blocking night time melatonin receptor mediated signaling pathways with increased concentrations of melatonin receptor antagonist, such as luzindole. Animals in 14:10 hours light:dark cycles were exposed to constant darkness and temperature (25° C.) for 4 days. On the $3^{rd}$ day of constant darkness, animals were treated with different concentrations of luzindole (0.5 μM, 1 μM, and 5 μM) at CT15 for one hour by bathing animals in the desired concentration of luzindole. Animals were then trained for active avoidance conditioning at CT16 and tested 24 hours later at CT16 on the $4^{th}$ day of constant darkness for long-term memory. FIG. 4a shows that the number of trials to learning remains the same, regardless of luzindole concentration. However, animals treated with increasing concentration of luzindole show a significant increase in long-term memory formation, as retention score increase from less than 0.1 with 0.5 μM luzindole, to 0.25 with 1 μM luzindole, to above 0.4 with 5 μM luzindole, as shown in FIG. 4b. These results demonstrate that blocking melatonin activated melatonin receptor signaling pathway during the subjective night does in fact block the inhibitory effect of melatonin during the night, phenocopying long-term memory formation for subjects trained during the subjective day. This means that day/night differences in memory consolidation following training for active avoidance conditioning was modulated by day/night differences in melatonin.

All references cited herein are incorporated by reference. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for improving memory in mammals including humans comprising:
   administering an effective amount of a melatonin receptor antagonist composition in a dose range between about 1 mg/kg to about 1000 mg/kg to an animal, including a human, within about an hour of commencing a cognitive learning activity and/or prior to going to sleep after engaging in a cognitive learning activity,
   where the effective amount is sufficient to reduce the inhibitory action of melatonin on long-term memory formation improving long-term memory formation and improving learned activity performance and outcomes,
   where the melatonin receptor composition comprises luzindole, K-185, or a mixture of luzindole and K-185, and
   where the cognitive learning activity includes studying for examinations, training of canines for use in civil and military applications, training of a task, where memory of data concerning the task is critical, training for a sport, training for military operations, training for police operations, training for police investigations, or in any other application where memory retention plays a role in successful performance of the task.

2. The method of claim 1, wherein the effective amount is increased to augment cognitive performance.

3. The method of claim 1, wherein melatonin receptor antagonist composition comprises luzindole.

4. The method of claim 1, wherein melatonin receptor antagonist composition comprises K-185.

5. The method of claim 1, wherein the effective amount is a dose range between about 1 mg/kg to about 500 mg/kg.

6. The method of claim 1, wherein the effective amount is a dose range between about 1 mg/kg to about 100 mg/kg.

7. The method of claim 1, wherein the effective amount is a dose range between about 5 mg/kg to about 100 mg/kg.

8. The method of claim 1, wherein the effective amount is a dose range between about 10 mg/kg to about 100 mg/kg.

9. The method of claim 1, wherein the effective amount is a dose range between about 20 mg/kg to about 100 mg/kg.

10. The method of claim 1, wherein the administration occurs within about 45 minutes prior to commencing the activity and/or going to sleep after the activity.

11. The method of claim 1, wherein the administration occurs within about 30 minutes prior to commencing the activity and/or going to sleep after the activity.

12. A method for improving memory in mammals including humans comprising:
   administering an effective amount of a melatonin receptor antagonist composition to an animal including a human within about an hour of commencing a cognitive learning activity and/or within an hour of going to sleep after commencing the cognitive learning activity improving learned activity performance and outcomes,
   where melatonin receptor antagonist composition comprises luzindole, K-185, or a mixture of luzindole and K-185,
   where the effective amount is sufficient to reduce the inhibitory action of melatonin on long-term memory formation improving long-term memory formation and improving learned activity performance and outcomes, at a dose range between about 1 mg/kg to about 1000 mg/kg, and
   where the cognitive learning activity include studying for examinations, training of canines for use in civil and military applications, training of a task, where memory of data concerning the task is critical, training for a sport, training for military operations, training for police operations, training for police investigations, or in any other application where memory retention plays a role in successful performance of the task.

13. The method of claim 12, wherein the effective amount is increased to augment cognitive performance.

14. The method of claim 12, wherein the administration occurs within about 45 minutes prior to commencing the activity and/or going to sleep after the activity and the effective amount is a dose range between about 1 mg/kg to about 500 mg/kg.

15. The method of claim 12, wherein the administration occurs within about 30 minutes prior to commencing the activity and/or going to sleep after the activity and the effective amount is a dose range between about 1 mg/kg to about 100 mg/kg.

16. The method of claim 12, wherein the administration occurs within about 30 minutes prior to commencing the activity and/or going to sleep after the activity and the effective amount is a dose range between about 5 mg/kg to about 100 mg/kg.

* * * * *